US012691231B2

(12) United States Patent
Tay

(10) Patent No.: US 12,691,231 B2
(45) Date of Patent: Jul. 28, 2026

(54) SAFETY INJECTION NEEDLE ASSEMBLY

(71) Applicant: Keng Kiong Tay, Kuching Sarawak (MY)

(72) Inventor: Keng Kiong Tay, Kuching Sarawak (MY)

( * ) Notice: Subject to any disclaimer, the term of this patent is extended or adjusted under 35 U.S.C. 154(b) by 960 days.

(21) Appl. No.: 17/641,398

(22) PCT Filed: Dec. 18, 2019

(86) PCT No.: PCT/MY2019/050114
§ 371 (c)(1),
(2) Date: Mar. 8, 2022

(87) PCT Pub. No.: WO2021/060965
PCT Pub. Date: Apr. 1, 2021

(65) Prior Publication Data
US 2022/0323692 A1       Oct. 13, 2022

(30) Foreign Application Priority Data
Sep. 26, 2019    (MY) ............................ PI2019005645

(51) Int. Cl.
*A61M 5/32*          (2006.01)
*A61M 5/50*          (2006.01)
(Continued)

(52) U.S. Cl.
CPC ........ *A61M 5/3275* (2013.01); *A61M 5/3213* (2013.01); *A61M 5/3293* (2013.01);
(Continued)

(58) Field of Classification Search
CPC .............. A61M 5/3275; A61M 5/3213; A61M 2005/3254; A61M 2205/273;
(Continued)

(56)            References Cited

U.S. PATENT DOCUMENTS 4,702,738 A * 10/1987 Spencer .............. A61M 5/3272
                                                        604/263
4,923,446 A * 5/1990 Page ................... A61M 5/3243
                                                        604/263
(Continued)

FOREIGN PATENT DOCUMENTS

EP            2870975  A1      5/2015
JP       2014/508002  A       4/2014
(Continued)

*Primary Examiner* — William R Carpenter
*Assistant Examiner* — Robert F Allen
(74) *Attorney, Agent, or Firm* — Alston & Bird LLP

(57)            ABSTRACT
The present invention relates to a safety injection needle assembly (100) comprising an injection needle (110) affixed to a hub (120) having a stud (130) and a receiving means (140) for receiving a dental syringe, an inner sheath (150) having a slit (190) to receive the stud (130) for retaining the injection needle (110), and an outer sheath (220) and a cap (240) for housing the inner sheath (150). In addition, a pair of outer studs (170) of the inner sheath (150) complements with an outer sheath inlet (230) and a cap inlet (250) for removably engaged and locked via locking means (210). The slit (190) comprises a plurality of terminal ends (200) for receiving and locking the stud (130) via the locking means (210). Preferably, the safety injection needle assembly (100) comprises a sealing member (260) having two set of indicators (280) for indicating position.

14 Claims, 5 Drawing Sheets

(51) Int. Cl.
　*A61M 39/10*　　(2006.01)
　*G09F 3/00*　　(2006.01)
(52) U.S. Cl.
　CPC ... *A61M 5/3202* (2013.01); *A61M 2005/3254*
　　(2013.01); *A61M 5/5086* (2013.01); *A61M*
　　*39/1011* (2013.01); *G09F 3/0292* (2013.01)
(58) Field of Classification Search
　CPC .............. A61M 5/3202; A61M 5/3271; A61M
　　5/3243; A61M 2005/3247; A61M 5/5086;
　　A61M 5/3293; A61M 39/1011; G09F
　　3/0292
　See application file for complete search history.

(56) References Cited

U.S. PATENT DOCUMENTS

| | | | | |
|---|---|---|---|---|
| 4,923,447 | A * | 5/1990 | Morgan | A61M 5/3271 |
| | | | | 604/263 |
| 5,222,945 | A * | 6/1993 | Basnight | A61M 5/3271 |
| | | | | 604/218 |
| 5,222,947 | A * | 6/1993 | D'Amico | A61M 5/3272 |
| | | | | 604/263 |
| 5,279,579 | A | 1/1994 | D'Amico | |
| 5,498,243 | A * | 3/1996 | Vallelunga | A61M 5/5066 |
| | | | | 604/207 |
| 5,562,625 | A * | 10/1996 | Stefancin, Jr. | A61M 5/3271 |
| | | | | 604/110 |
| 5,591,138 | A * | 1/1997 | Vaillancourt | A61M 5/3271 |
| | | | | 604/263 |
| 6,302,868 | B1 * | 10/2001 | Mohammad | A61B 5/153 |
| | | | | 604/195 |
| 6,379,337 | B1 * | 4/2002 | Mohammad | A61B 5/150633 |
| | | | | 604/162 |
| 6,669,671 | B1 * | 12/2003 | Mohammad | A61M 5/3232 |
| | | | | 604/196 |
| 6,776,775 | B1 * | 8/2004 | Mohammad | A61B 5/150572 |
| | | | | 604/264 |
| 7,141,286 | B1 * | 11/2006 | Kessler | A61M 5/3202 |
| | | | | 215/230 |
| 2002/0107489 | A1 * | 8/2002 | Lee | A61M 5/3243 |
| | | | | 604/197 |
| 2003/0093035 | A1 * | 5/2003 | Mohammed | A61M 5/3257 |
| | | | | 604/195 |
| 2003/0125677 | A1 * | 7/2003 | Swenson | A61B 17/205 |
| | | | | 128/919 |
| 2005/0228345 | A1 * | 10/2005 | Yang | A61M 5/3271 |
| | | | | 604/110 |
| 2005/0267416 | A1 * | 12/2005 | Mohammed | A61M 5/3272 |
| | | | | 128/919 |
| 2006/0100589 | A1 * | 5/2006 | Lin | A61M 5/3243 |
| | | | | 604/198 |
| 2006/0178639 | A1 * | 8/2006 | Eric | A61M 5/3243 |
| | | | | 604/192 |
| 2006/0282044 | A1 * | 12/2006 | Mohammed | A61B 5/150717 |
| | | | | 604/192 |
| 2012/0061274 | A1 * | 3/2012 | Tumminello | A61B 17/06128 |
| | | | | 53/477 |
| 2015/0038903 | A1 | 2/2015 | Jensen et al. | |
| 2015/0126939 | A1 * | 5/2015 | Quinn | A61M 5/3271 |
| | | | | 604/198 |
| 2017/0007771 | A1 * | 1/2017 | Duinat | A61M 5/3137 |
| 2017/0143912 | A1 * | 5/2017 | Hu | A61M 5/3202 |
| 2019/0001070 | A1 * | 1/2019 | Wendland | A61M 5/3202 |
| 2019/0167911 | A1 * | 6/2019 | Rassouli | A61M 5/345 |

FOREIGN PATENT DOCUMENTS

| | | | | | |
|---|---|---|---|---|---|
| KR | 10-2018-0103496 | * | 9/2018 | .......... | A61M 5/3202 |
| KR | 10-2018-0103496 A1 | | 9/2018 | | |
| WO | WO 2013/048310 A1 | | 4/2013 | | |

* cited by examiner (a)                          (b)                          (c)

SAFETY INJECTION NEEDLE ASSEMBLY

CROSS-REFERENCE TO RELATED APPLICATIONS

This application is a national stage entry of International Application No. PCT/MY2019/050114 filed Dec. 18, 2018, which claims the benefit of Malaysian Application No. PI2019005645 filed Sep. 26, 2019.

TECHNICAL FIELD

The present invention generally relates to a safety injection needle assembly and more particularly to a safety injection needle assembly for use in the field of dentistry to prevent accidental needlestick injury.

BACKGROUND ART

Injection needle is widely used for administering a drug such as an anesthetic drug to a person. For an example, a dental anesthetic is given by injection using a dental injection needle. However, most dental injection needle lacks safety features to prevent accidental needle stick injuries, which carry the risk of transmitting blood borne diseases such as human immunodeficiency viruses (HIV) and Hepatitis B.

There are few dental injection needles with safety-enhanced features but these injection needles are either too expensive or not user friendly. Further, there have been a number of solutions that provide a dental injection needle with an enhanced safety feature and two of them are discussed below:

WO 2012000837 A1 disclosed an injection device comprising a safety device and a pre-filled syringe having a hypodermic needle. The safety device comprises a support body, an outer body, a needle shield, a releasable retaining means and a guiding means having a guide pin. The prior art involves moving the needle shield into a plurality of positions that comprises a locking mechanisms to control the desired movement and position of the needle shield, which in turn, control the exposure of the hypodermic needle. However, the prior art only provides a permanent locking mechanism, where there is no option for a temporary locking mechanism to further control the position and movement of the needle shield. Further, the pre-filled syringe is configured to be retained within the safety device in order for the prior art to work, which may not be suitable for injection at narrow or less accessible part such as the posterior gums.

U.S. Pat. No. 9,789,262 B2 relates to a protective sheath for a cannula to prevent or minimize accidental needlestick injuries. The protective sheath is arranged on a hub and can be fitted with a dental syringe, in which the protective sheath comprises a hollow cylindrical body having cavities, forming a female feature configured to cooperate with a male element of the hub for guiding movement of the sheath into a plurality of retracted positions. More particularly, the female feature comprises a primary, secondary and tertiary transition structure to receive the male element of the hub and guide the male element to their respective positions; a primary and secondary locking structure that temporarily lock the male element in its respective position; a final locking structure that permanently lock the male element in its respective position; and a guiding structure to guide the male element to the desired position. However, the prior art does not have an outer sheath that envelops the whole protective sheath having an injection needle to further ensure sterility and better protection against needlestick injuries. Further, the prior art does not comprise a means to indicate the position of the male element and the locking structure for easy reference by the user.

Accordingly, it can be seen in the prior arts that there exists a need to have an improved and more efficient safety injection needle assembly that provides different types of locking means at different positions to obtain the desired exposure of the injection needle during an injection. In addition, there exists a need to optimize the safety and sterility of the injection needle by having a double layer sheath. Further, itis desirably to have an indicator for indicating the position and locking means for convenience of the user.

SUMMARY OF THE INVENTION

The following presents a simplified summary of the invention in order to provide a basic understanding of some aspects of the invention. This summary is not an extensive overview of the invention. Its sole purpose is to present some concepts of the invention in a simplified form as a prelude to the more detailed description that is presented later.

An objective of the present invention is to provide a more user-friendly safety injection needle assembly, preferably for application in dentistry field.

It is also an objective of this invention to provide a safety injection needle assembly having a double safety protection for user against accidental needlestick injuries and sterility of the injection needle by having a double layer sheath, more particularly to an inner sheath for housing the injection needle and an outer sheath for fully enveloping the inner sheath that housing the injection needle.

A further objective of the present invention is to provide a safety injection needle assembly comprising a slit on the inner sheath for receiving a stud, in which the slit having a plurality of terminal ends to control exposure of the injection needle by gliding the stud within the slit to a desired position.

Another objective of the present invention is to provide a safety injection needle assembly having a locking means, more particularly to a temporary locking means and a permanent locking means for efficiently holding and locking the injection needle at the desired position such as at the respective plurality of terminal ends on the inner sheath.

It is a further objective of the present invention to provide a safety injection needle assembly having an outer sheath and a cap. Further, both of the outer sheath and the cap having an inlet and a locking means, more particularly to a temporary locking means and a permanent locking means, for locking the outer sheath and the cap with the inner sheath via a pair of outer studs of the inner sheath and the respective inlets of the outer sheath and the cap.

In addition, another objective of the present invention is to provide a safety injection needle assembly having a tearable sealing member which comprises two set of indicators for indicating the position of the pair of outer studs and the pair of inlets on the outer sheath, the cap and the permanent locking means comprised on the safety injection needle assembly.

Accordingly, these objectives may be achieved by following the teachings of the present invention. The present invention relates to a safety injection needle assembly to prevent accidental needlestick injuries, comprising an injection needle affixed to a hub having a stud and a receiving means for receiving a conventional dental syringe, an inner sheath having a slit to receive the stud for retaining the injection needle, and an outer sheath and a cap for housing the inner sheath comprising the injection needle. In addition, a pair of outer studs of the inner sheath complements with an outer sheath inlet and a cap inlet to removably engage and lock the inner sheath with the outer sheath and the cap via a locking means. Further, the slit of the inner sheath comprises a plurality of terminal ends for receiving and locking the stud via the locking means. Preferably, the safety injection needle assembly comprises a sealing member having two set of indicators for indicating the position of the outer sheath inlet, the cap inlet, the pair of outer studs and a permanent locking means.

The foregoing and other objects, features, aspects and advantages of the present invention will become better understood from a careful reading of a detailed description provided herein below with appropriate reference to the accompanying drawings.

BRIEF DESCRIPTION OF THE ACCOMPANYING DRAWINGS

So that the manner in which the above recited features of the present invention can be understood in detail, a more particular description of the invention, briefly summarized above, may have been referred by embodiments, some of which are illustrated in the appended drawings. It is to be noted, however, that the appended drawing illustrates only typical embodiments of this invention and are therefore not to be considered limiting of its scope, for the invention may admit to other equally effective embodiments.

These and other features, benefits, and advantages of the present invention will become apparent by reference to the following text figure, with like reference numbers referring to like structures across the views, wherein.

Figures 5A, 5B:
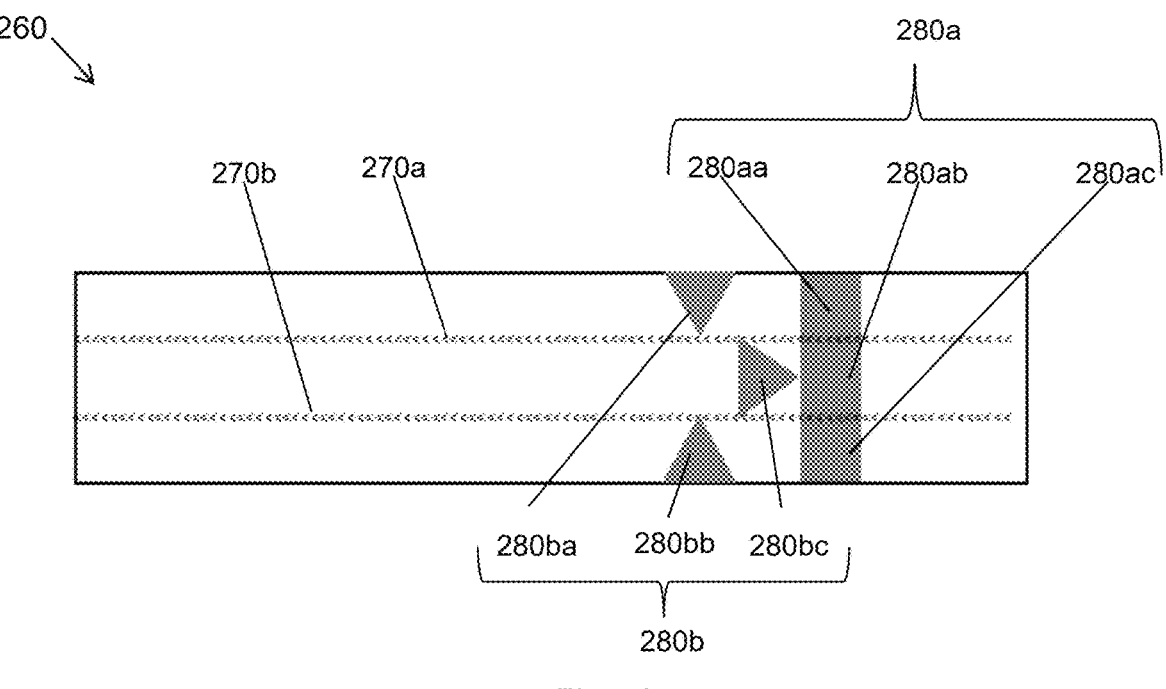

FIGS. 5A-B are a schematic diagram illustrating a sealing member of the safety injection needle assembly in (A) a pre-use position and (B) an end-use position in accordance to a preferred embodiment of the present invention.

Figure 6A:
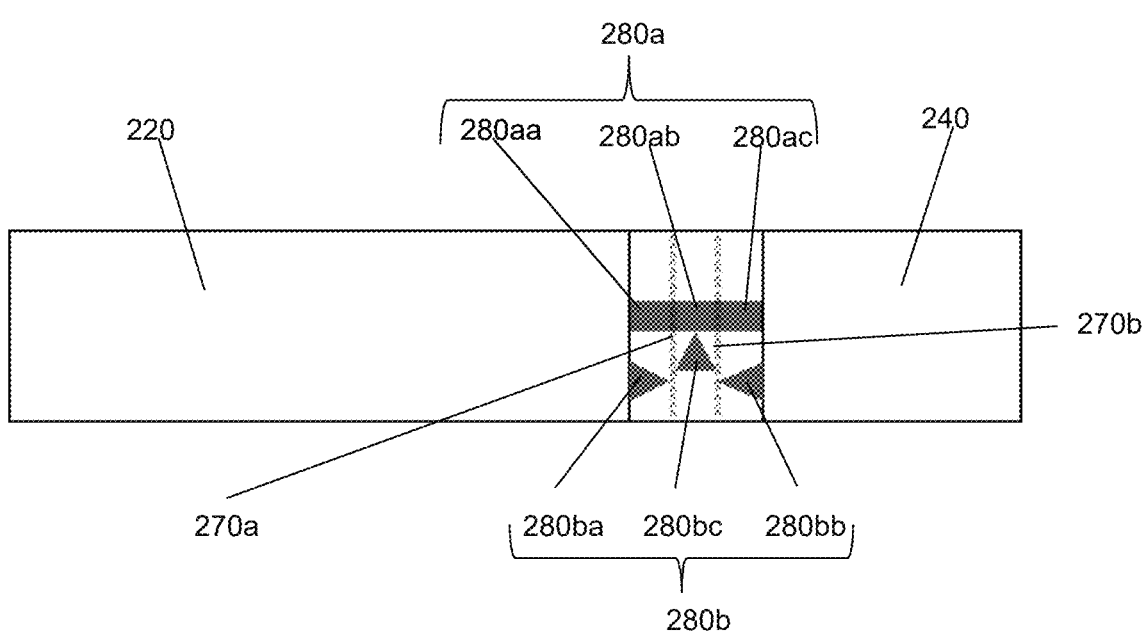
Figure 6B:
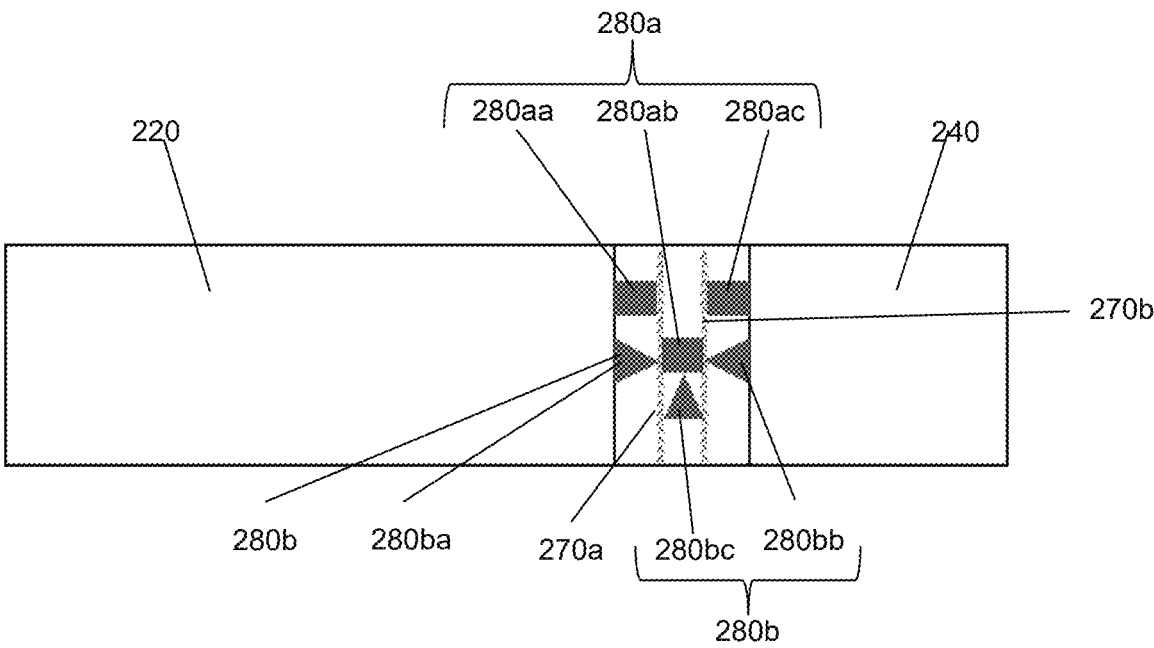

FIGS. 6A-B are a schematic diagram illustrating the sealing member encircles the safety injection needle assembly in (A) the pre-use position and (B) the end-use position in accordance to a preferred embodiment of the present invention.

DETAILED DESCRIPTION OF THE PREFERRED EMBODIMENTS

While the present invention is described herein by way of example using embodiments and illustrative drawings, those skilled in the art will recognize that the invention is not limited to the embodiments of drawing or drawings described, and are not intended to represent the scale of the various components. Further, some components that may form a part of the invention may not be illustrated in certain figures, for ease of illustration, and such omissions do not limit the embodiments outlined in any way. It should be understood that the drawings and detailed description thereto are not intended to limit the invention to the particular form disclosed, but on the contrary, the invention is to cover all modifications, equivalents, and alternatives falling within the scope of the present invention as defined by the appended claim. As used throughout this description, the word "may" is used in a permissive sense (i.e. meaning having the potential to), rather than the mandatory sense, (i.e. meaning must). Further, the words "a" or "an" mean "at least one" and the word "plurality" means "one or more" unless otherwise mentioned. Furthermore, the terminology and phraseology used herein is solely used for descriptive purposes and should not be construed as limiting in scope. Language such as "including," "comprising," "having," "containing," or "involving," and variations thereof, is intended to be broad and encompass the subject matter listed thereafter, equivalents, and additional subject matter not recited, and is not intended to exclude other additives, components, integers or steps. Likewise, the term "comprising" is considered synonymous with the terms "including" or "containing" for applicable legal purposes.

Any discussion of documents, acts, materials, devices, articles and the like is included in the specification solely for the purpose of providing a context for the present invention. It is not suggested or represented that any or all of these matters form part of the prior art base or were common general knowledge in the field relevant to the present invention.

In this disclosure, whenever a composition or an element or a group of elements is preceded with the transitional phrase "comprising", it is understood that we also contemplate the same composition, element or group of elements with transitional phrases "consisting of", "consisting", "selected from the group of consisting of, "including", or "is" preceding the recitation of the composition, element or group of elements and vice versa.

The present invention is described hereinafter by various embodiments with reference to the accompanying drawing, wherein reference numerals used in the accompanying drawing correspond to the like elements throughout the description. This invention may, however, be embodied in many different forms and should not be construed as limited to the embodiment set forth herein. Rather, the embodiment is provided so that this disclosure will be thorough and complete and will fully convey the scope of the invention to those skilled in the art. In the following detailed description, numeric values and ranges are provided for various aspects of the implementations described. These values and ranges are to be treated as examples only and are not intended to limit the scope of the claims. In addition, a number of materials are identified as suitable for various facets of the implementations. These materials are to be treated as exemplary and are not intended to limit the scope of the invention.

The present invention relates to a safety injection needle assembly (100), the safety injection needle assembly (100) comprising: an injection needle (110) affixed to a hub (120) having a stud (130) and a receiving means (140) for receiving a syringe, whereby the hub (120) is affixed at a distal end of an injection site of the injection needle (110); an inner sheath (150) having a slit (190) for receiving the stud (130), thereby positioning and retaining the injection needle (110) within the inner sheath (150); and an outer sheath (220) and a cap (240) for housing the inner sheath (150) comprising the injection needle (110); characterized in that, the inner sheath (150) having a pair of outer studs (170), the outer sheath (220) having an outer sheath inlet (230) and the cap (240) having a cap inlet (250) that complement with the pair of outer studs (170), thereby removably engage and lock the inner sheath (150) with the outer sheath (220); and wherein the slit (190) of the inner sheath having a plurality of terminal ends (200a, 200b, 200c) for receiving the stud (130) to position the injection needle (110) and locking the stud (130) to retain the injection needle (110).

Referring to the drawings as shown in FIG. 1 to FIG. 6, the invention will now be described in more detail.

Figure 1:
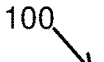
FIG. 1 is a schematic diagram illustrating a safety injection needle assembly in accordance to a preferred embodiment of the present invention.
Figure 1:
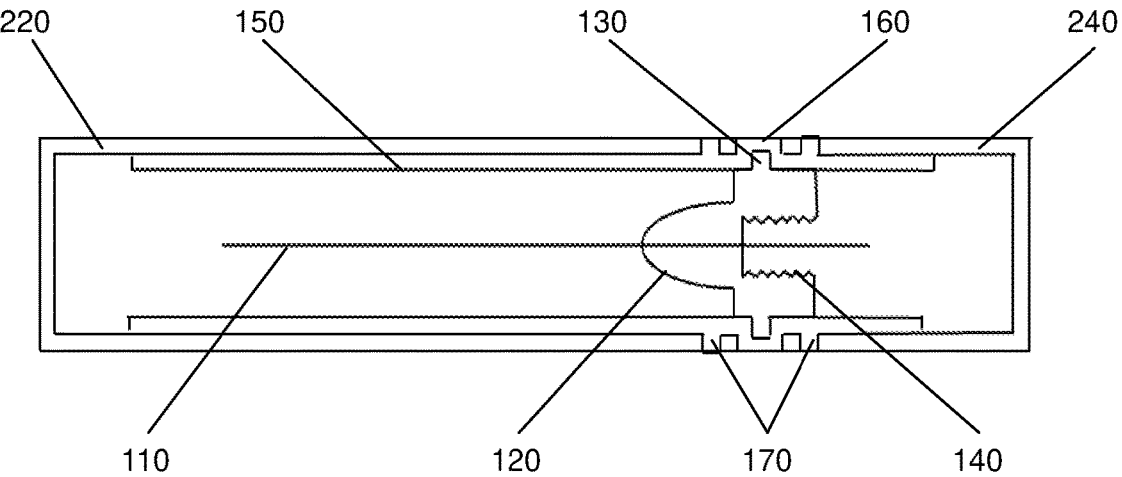

FIG. 1 is a schematic diagram illustrating the safety injection needle assembly (100) in accordance to a preferred embodiment of the present invention. The safety injection needle (100) comprises the injection needle (110), the inner sheath (150) for housing the injection needle (110), and the outer sheath (220) and the cap (240) for housing the inner sheath having the injection needle (110). The injection needle (110) is affixed to the hub (120) having the stud (130) and the receiving means (140). More particularly, the injection needle (110) is preferably a conventional injection needle and the hub (120) is affixed at a distal end of an injection site of the injection needle (110). Preferably, the receiving means (140) is, but not limited to, a screw thread, which is configured to receive the syringe, more particularly to a conventional dental syringe. Further, the stud (130) of the hub (120) is removably engaged with the inner sheath (150), more particularly, via the slit (190) comprised on the inner sheath (150), for positioning and retaining the injection needle (110) within the inner sheath (150).

In accordance with an embodiment of the present invention, the inner sheath (150) having the pair of outer studs (170), the outer sheath (220) having the outer sheath inlet (230) and the cap (240) having the cap inlet (250) that complement with the pair of outer studs (170), thereby removably engage and lock the inner sheath (150) with the outer sheath (220).

In accordance with an embodiment of the present invention, the inner sheath (150) having a protruding surface (160) located between the pair of outer studs (170).

Figure 2:
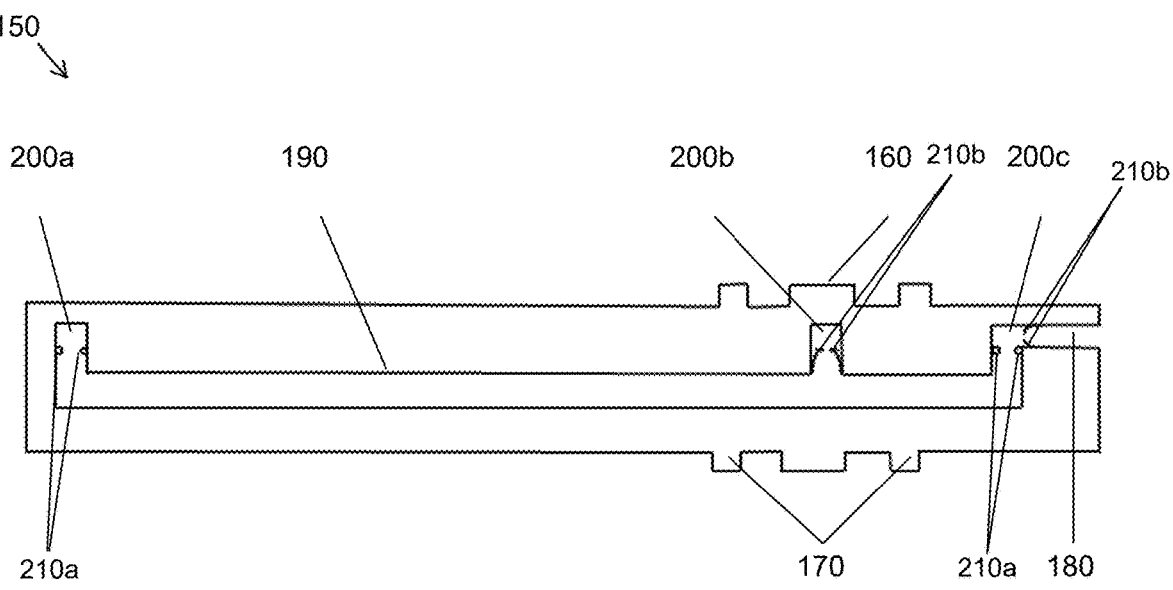
FIG. 2 is a schematic diagram illustrating an inner sheath of the safety injection needle assembly in accordance to a preferred embodiment of the present invention.

FIG. 2 is a schematic diagram illustrating the inner sheath (150) of the safety injection needle assembly (100) in accordance to a preferred embodiment of the present invention. The inner sheath (150) comprising the slit (190) having the plurality of terminal ends (200a, 200b, 200c) for receiving the stud (130) to position the injection needle (110) and locking the stud (130) to retain the injection needle (110). In the pre-use position, which is prior to usage of the injection needle (110), the stud (130) was positioned at the temporary locking means (210a) of the third terminal end (200c) that is aligned with a stud inlet (180).

In accordance with an embodiment of the present invention, the inner sheath (150) comprising the stud inlet (180) for receiving the stud (130), connected to the slit (190) of the inner sheath (150).

In accordance with an embodiment of the present invention, the plurality of terminal ends (200a, 200b, 200c) of the slit (190) including a first terminal end (200a), a second terminal end (200b) and a third terminal end (200c), whereby each of the first terminal end (200a), the second terminal end (200b) and the third terminal end (200c) of the inner sheath (150) having a locking means (210a, 210b) for locking the stud (130). Further, each of the plurality of terminal ends (200a, 200b, 200c) determines the position of the injection needle (110), more particularly to the exposure of the injection needle (110).

In accordance with an embodiment of the present invention, the first terminal end (200a) located at a distal end from the stud inlet (180) and the pair of outer studs (170) of the inner sheath (150).

In accordance with an embodiment of the present invention, the third terminal end (200c) located at a proximal end from the pair of outer studs (170) of the inner sheath (150). Further, the stud inlet (180) is located adjacent to the third terminal end (200c) of the slit (190).

In accordance with an embodiment of the present invention, the second terminal end (200b) located between the first terminal end (200a) and the third terminal end (200c).

Figure 3:
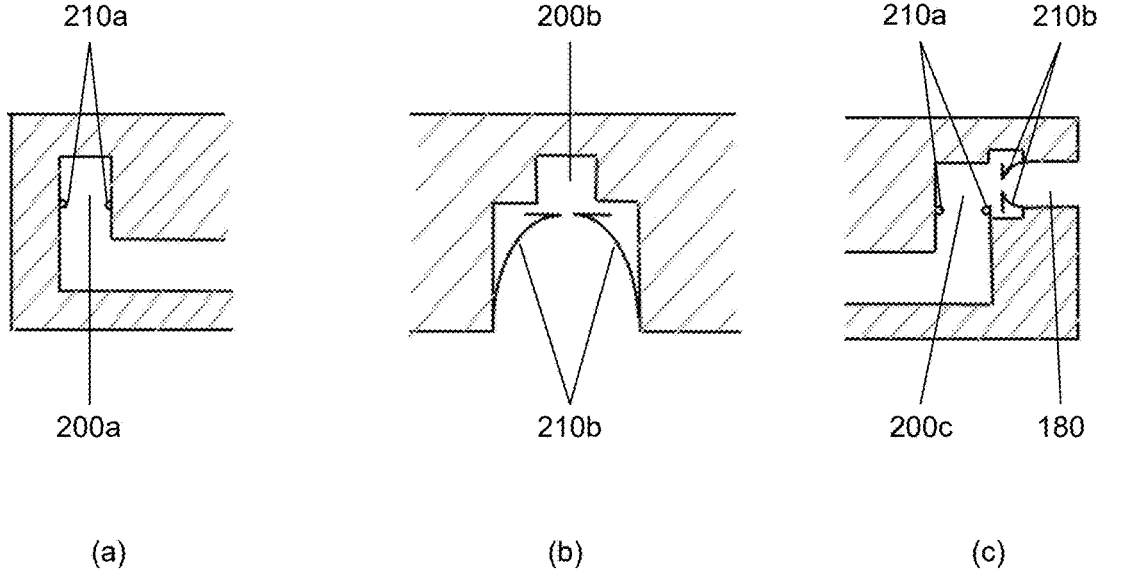
FIG. 3 is a schematic diagram illustrating a locking means on (a) a first terminal end; (b) a second terminal end; and (c) a third terminal end and a stud inlet of the inner sheath in accordance to a preferred embodiment of the present invention.

FIG. 3 is a schematic diagram illustrating the locking means (210a, 210b) on (a) the first terminal end (200a); (b) the second terminal end (200b); and (c) the third terminal end (200c) and the stud inlet (180) of the inner sheath (150) in accordance to a preferred embodiment of the present invention. Preferably, the locking means (210a, 210b) including a temporary locking means (210a) and a permanent locking means (210b).

In accordance with an embodiment of the present invention, the temporary locking means (210a) comprising a plurality of projections. In addition, the permanent locking means (210b) comprising a unidirectional lock. Further, as shown in FIG. 3(a) to (c), the temporary locking means (210a) preferably comprises, but not limited to, a plurality of semicircular projections, while the permanent locking means (210b) preferably comprises, but not limited to, a pair of L-shaped spring locks.

In accordance with an embodiment of the present invention, each of the first terminal end (200a) and the third terminal end (200c) of the inner sheath (150) preferably having the temporary locking means (210a) for locking and unlocking the stud (130).

More particularly, the temporary locking means (210a) on the first terminal end (200a) is configured to retain the stud (130) to fully expose the injection needle (110) from the inner sheath (150). On the other hand, the temporary locking means (210a) on the third terminal end (200c) is configured to fully cover the injection needle (110) within the inner sheath (150).

In accordance with an embodiment of the present invention, the stud inlet (180) and the second terminal end (200b) preferably having the permanent locking means (210b) for locking the stud (130). More particularly, the permanent locking means (210b) on the stud inlet (180) is configured to retain the stud (130) on the slit (190), while the permanent locking means (210b) on the terminal end (200b) is configured to retain the stud (130) at an end-use position, specifically at the end of usage of the injection needle (110) for disposal.

Figure 4:
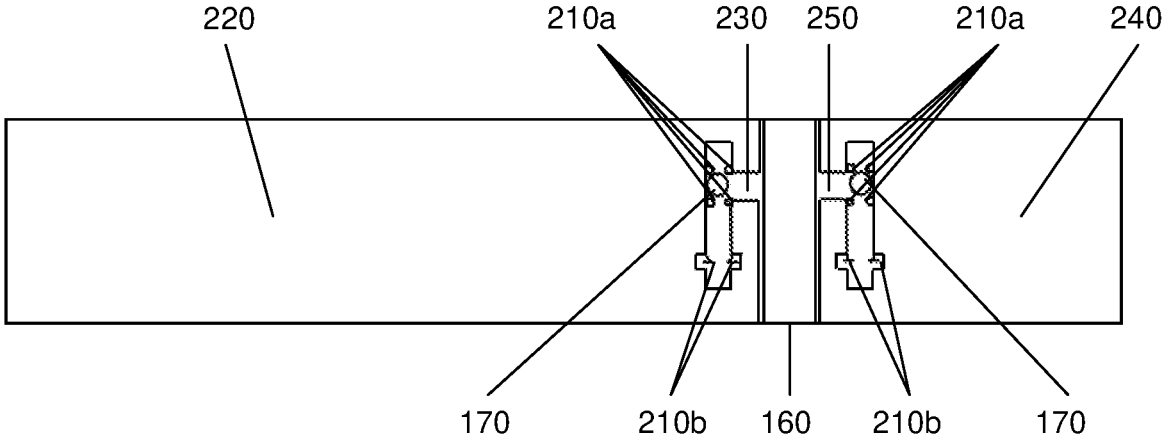
FIG. 4 is a schematic diagram illustrating an attachment of an outer sheath and a cap to the inner sheath of the safety injection needle assembly in accordance to a preferred embodiment of the present invention.

FIG. 4 is a schematic diagram illustrating an attachment of the outer sheath (220) to the inner sheath (150) of the safety injection needle assembly (100) in accordance to a preferred embodiment of the present invention. As shown in FIG. 4, the outer sheath (220) is configured to house the inner sheath (150) comprising the injection needle (110). Preferably, the outer sheath (220) and the cap (240) are housing a different part of the inner sheath (150).

In accordance with an embodiment of the present invention, the cap (240) is configured to house the inner sheath (150) having the receiving means (140) of the hub (120). On the other hand, the outer sheath (220) is configured to house the inner sheath (150) having the injection site of the injection needle (110). Preferably, the outer sheath (220) and the cap (240) are removably housing the inner sheath (150) depending on a user requirement.

In accordance with an embodiment of the present invention, the outer sheath (220) and the cap (240) are separated by the protruding surface (160) of the inner sheath (150) in the pre-use position.

As shown in FIG. 4, each of the outer sheath inlet (230) and the cap inlet (250) comprising the temporary locking means (210*a*) and the permanent locking means (210*b*) for locking the pair of outer studs (170) of the inner sheath (150) to the outer sheath (220) and the cap (240). Similar to the inner sheath (150), the temporary locking means (210*a*) of the outer sheath (220) and the cap (240) preferably comprises, but not limited to, the plurality of semicircular projections, while the permanent locking means (210*b*) of the outer sheath (220) and the cap (240) preferably comprises, but not limited to, the pair of L-shaped spring locks.

Preferably, both of the outer sheath inlet (230) and the cap inlet (250) are T-shaped inlets. More preferably, the temporary locking means (210*a*) is located at the junction of the T-shaped inlet, the permanent locking means (210*b*) is located at one end of the T-shaped inlet, while the opposite end of the T-shaped inlet does not have a locking means (210*a*, 210*b*). Further, in the pre-use position, the pair of outer studs (170) were aligned and secured at the temporary locking means (210*a*) of the respective outer sheath inlet (230) and the cap inlet (250).

More particularly, the temporary locking means (210*a*) on the outer sheath inlet (230) and the cap inlet (250) is configured to retain the respective outer studs (170) in the pre-use position, whereas the permanent locking means (210*b*) on the outer sheath inlet (230) and the cap inlet (250) is configured to retain the respective outer studs (170) in the end-use position. Further, the safety injection needle assembly (100) is safely disposed once both of the inner sheath (150) and the outer sheath (220) are in the end-use position.

FIGS. 5A-B are a schematic diagram illustrating a sealing member (260) of the safety needle assembly (100) in (A) the pre-use position and (B) the end-use position in accordance to a preferred embodiment of the present invention. More particularly, the injection needle assembly (100) comprising the sealing member (260) having a pair of tearable serrated lines (270*a*, 270*b*), which is referred as a first serrated line (270*a*) and a second serrated line (270*b*).

In accordance with an embodiment of the present invention, the sealing member (260) having, but not limited to, two set of indicators (280*a*, 280*b*) for indicating position of the outer sheath inlet (230), the cap inlet (250), the pair of outer studs (170) within the outer sheath inlet (230) and the cap inlet (250), the permanent locking means (210*b*) and the second terminal end (200*b*).

In accordance with an embodiment of the present invention, the injection needle assembly (100) comprising the sealing member (260) having the pair of tearable serrated lines (270*a*, 270*b*) as an outermost layer, encircling the protruding surface (160) of the inner sheath (150), the outer sheath (220) and the cap (240) in the pre-use position. FIG. 6 is a schematic diagram illustrating the sealing member (260) encircles the safety injection needle assembly (100) in (a) the pre-use position and (b) the end-use position in accordance to a preferred embodiment of the present invention.

In accordance with an embodiment of the present invention, the sealing member (260) is preferably tearable into three sections along the pair of serrated lines (270*a*, 270*b*), whereby the three sections are separately attached on the protruding surface (160) of the inner sheath (150), the outer sheath (220) and the cap (240) as shown in FIG. 6.

In accordance with an embodiment of the present invention, the first set of indicators (280*a*) comprised on the sealing member (260) having three markings, whereby the three markings correspond to the position of the outer sheath inlet (230), the pair of outer studs (170) and the cap inlet (250). As shown in FIGS. 5A-B and 6A-B, the three markings are preferably, but not limited to three rectangular markings, namely a first marking (280*aa*), a second marking (280*ab*), and a third marking (280*ac*). More particularly, the first marking (280*aa*), the second marking (280*ab*) and the third marking (280*ac*) correspond to the position of the outer sheath inlet (230), the pair of the outer studs (170), and the cap inlet (250), respectively.

Preferably, the first marking (280*aa*), the second marking (280*ab*), and the third marking (280*ac*) are aligned when in the pre-use position as shown in FIG. 5A and FIG. 6A. An alignment of the first marking (280*aa*) and the second marking (280*ab*) corresponds to an alignment of the outer sheath inlet (230) with the respective outer stud (170), enabling placement or removal of the outer sheath (220) on the inner sheath (150). Further, an alignment of the second marking (280*ab*) and the third marking (280*ac*) corresponds to an alignment of the cap inlet (250) with the respective outer stud (170), enabling placement or removal of the cap (240) on the inner sheath (150).

In accordance with an embodiment of the present invention, the second set of indicators (280*b*) comprised on the sealing member (260) having three markings, whereby the three markings correspond to the permanent locking means (210*b*) on the outer sheath (220), the cap (240) and on the second terminal end (200*b*). In the end-use position, the position of the stud (130) is verified when the hub (120) is overlaid by the second set of indicators (280*b*) as shown in FIG. 6(*b*).

As shown in FIGS. 5A-B and FIGS. 6A-B, the three markings of the second set of indicators (280*b*) are preferably, but not limited to three triangular pointers, namely a first pointer (280*ba*), a second pointer (280*bb*), and a third pointer (280*bc*). Preferably, the first pointer (280*ba*) corresponds to the permanent locking means (210*b*) comprised on the outer sheath (220), specifically on the outer sheath inlet (230). The second pointer (280*bb*) corresponds to the permanent locking means (210*b*) comprised on the cap (240), specifically on the cap inlet (250). Further, the third pointer (280*bc*) corresponds to the permanent locking means (210*b*) comprised on the inner sheath (150), specifically on second terminal end (200*b*).

More particularly, an alignment of the first pointer (280*ba*) with the second marking (280*ab*) indicates that the respective outer stud (170) is locked in the permanent locking means (210*b*) comprised on the outer sheath inlet (230). On the other hand, an alignment of the second pointer (280*bb*) with the second marking (280*ab*) indicates that the respective outer stud (170) is locked in the permanent locking means (210*b*) comprised on the cap inlet (250).

As shown in FIG. 5B and FIG. 6B, the second set of indicators (280*b*) is pointing towards the second marking (280*ab*), indicating that the pair of outer studs (170) is locked in the permanent locking means (210*b*) on the respective outer sheath inlet (230) and the cap inlet (250), and the stud (130) is also locked in the permanent locking means (210*b*) on the second terminal ends (200*b*) of the inner sheath (150). Preferably, when the second set of indicators (280*b*) is in the end-use position, the injection needle (110) is fully covered and permanently locked within the inner sheath (150) and hence the safety injection needle assembly (100) can be safely disposed.

Preferably, the stud (130), the pair of outer studs (170), the stud inlet (180), the slit (190), the plurality of terminal ends (200*a*, 200*b*, 200*c*), the locking means (210*a*, 210*b*), the pair of inlets (250) and the two set of indicators (280*a*, 280*b*) can either present and function independently or as a mirror-image pair.

Hereinafter, example of the present invention will be provided for more detailed explanation. The advantages of the present invention may be more readily understood and put into practical effect from these examples. However, it is to be understood that the following examples are not intended to limit the scope of the present invention in any way.

EXAMPLES

Example 1

Affixing Syringe to the Safety Injection Needle Assembly

The safety injection needle assembly (100) in the pre-use position was selected for the injection operation, in which the safety injection needle assembly (100) was held in a position that the outer sheath (220) was on the left side while the cap (240) was on the right side. In the pre-use position, the pair of outer studs (170) were aligned and secured at the temporary locking means (210*a*) of the respective outer sheath inlet (230) and the cap inlet (250). Further, the first marking (280*aa*), the second marking (280*ab*) and the third marking (280*ac*) of the first set of indicators (280*a*) was also aligned in the pre-use position.

The cap (240) was twisted gently to tear the sealing member (260) along the second serrated line (270*b*), resulting in the respective outer stud (170) to move toward the opposite end of the permanent locking means (210*b*) of the T-shaped cap inlet (250) that has no locking means (210*a*, 210*b*). As a result, the third marking (280*ac*) of the sealing member (260) moved counterclockwise from its pre-use position, hence no longer aligned with the first marking (280*aa*) and the second marking (280*ab*). The non-aligned third marking (280*ac*) indicates that the position of the outer stud (170) within the cap inlet (250) is no longer aligned with the outer stud (170) within the outer sheath inlet (230), in which the outer stud (170) already moved upwards to the opposite end of the permanent locking means (210*b*) of the T-shaped cap inlet (250).

After the sealing member (260) was torn along the second serrated line (270*b*), the cap (240) was turned clockwise until the third marking (280*ac*) was aligned with the second marking (280*ab*) again to indicate that the outer stud (170) was aligned with the cap inlet (250), namely the outer stud (170) was at the pre-use position again, and followed by removing the cap (240) from the inner sheath (150).

A dental syringe was affixed to the safety injection needle assembly (100) via the receiving means (140) on the hub (120). The stud (130) was held in the pre-use position, where the stud (130) was locked at the temporary locking means (210*a*) of the third terminal end (200*c*) of the slit (190).

The outer sheath (220) was then twisted gently to tear the sealing member (260) along the first serrated line (270*a*), resulting in the first marking (280*aa*) of the sealing member (260) moved from its pre-use position and hence no longer aligned with the second marking (280*ab*). The outer stud (170) was then realigned with the outer sheath inlet (230)

again to the pre-use position, followed by removing the outer sheath (220) from the inner sheath (150). Hence, both of the outer sheath (220) and cap (240) were removed from being engaged with the inner sheath (150) while the injection needle (110) remains within the inner sheath (150).

Example 2

Injection Operation Using the Safety Injection Needle Assembly

In the pre-use position, the stud (130) was positioned at the temporary locking means (210*a*) of the third terminal end (200*c*). The inner sheath (150) was turned clockwise to release the stud (130) from the temporary locking means (210*a*) of the third terminal end (200*c*), enabling the stud (130) to glide up and down the slit (190). The injection needle (110) was fully exposed when the stud (130) glided to the first terminal end (200*a*). Further, the stud (130) was temporarily locked at the temporary locking means (210*a*) of the first terminal end (200*a*), hence preventing the inner sheath (150) from moving and interfering with the injection operation.

After the injection, the inner sheath (150) was turned clockwise to release from the temporary locking means (210*a*) of the first terminal end (200*a*). The stud (130) was glided towards the third terminal end (200*c*), resulting in the injection needle (110) to be fully covered in the inner sheath (150) Further, the stud (130) can be glided repeatedly along the slit (190) depending on the user requirement, hence allowing multiple injections to be performed using the same injection needle (110).

Example 3

Disposal of the Safety Injection Needle Assembly

Once the injection operation was completed, the stud (130) was glided along the slit (190) and moved into the permanent locking means (210*b*) of the second terminal end (200*b*), in which the stud (130), the permanent locking means (210*b*) and the second terminal ends (200*b*) were overlaid by the second marking (280*ab*) and the third pointer (280*bc*), corresponding to the end-use position. By turning the inner sheath (150) counterclockwise, the inner sheath (150) and the hub (120) were locked securely together into a single unit in the end-use position.

In the end-use position, the outer sheath (220) was then engaged with the inner sheath (150) again prior to disposal of the safety injection needle sheath (100). The first marking (280*aa*) and the second marking (280*ab*) were aligned, resulted in the alignment of the outer stud (170) with the outer sheath inlet (230), and followed by pushing the respective outer stud (170) into the outer sheath inlet (230). Subsequently, it resulted in a snug-fitting between the inner sheath (150) and the outer sheath (220). Further, the outer sheath (220) was turned clockwise and the outer stud (170) was then pushed into the permanent locking means (210*b*) of the outer sheath inlet (230), which can be verified when the first pointer (280*ba*) aligned with the second marking (280*ab*).

The injection needle (110) was then dismounted from the syringe by unscrewing the syringe at the receiving means (140), followed by engaging the cap (240) with the inner sheath (150) again. Similar to when engaging the outer sheath (220) to the inner sheath (150, the second marking (280*ab*) and the third marking (280*ac*) were aligned and pushed towards each other, resulted in the alignment of the outer stud (170) with the cap inlet (250) and the outer stud (170) being pushed into the cap inlet (250). Subsequently, it resulted in a snug-fitting between the inner sheath (150) and the cap (240). Further, the cap (240) was turned clockwise and hence the outer stud (170) was pushed into the permanent locking means (210*b*) of the cap inlet (250), which can be verified when the second pointer (280*bb*) pointed to the second marking (280*ab*). Hence, the inner sheath (150) was fully engaged by the outer sheath (220) and the safety injection needle assembly (100) can be disposed without getting accidental needlestick injuries.

The above-mentioned safety injection needle assembly (100) overcomes the problems and shortcomings of the existing injection needle assembly. The present invention is more user-friendly and provides a double safety protection for user accidental needlestick injuries and sterility of the injection needle by having a double layer sheath (150, 220), more particularly to the inner sheath (150) for housing the injection needle, and the outer sheath (220) and the cap (240) for fully envelop the inner sheath (150) which housing the injection needle (110). In addition, the present invention allows the user to control exposure of the injection needle (110) by gliding the stud (130) within the slit (190) having the plurality of terminal ends (200*a*, 200*b*, 200*c*). Further, the present invention also provides locking means (210*a*, 210*b*) including temporary locking means (210*a*) and permanent locking means (210*b*) for efficiently holding the injection needle (110) at the desired position by locking the stud (130) at the respective plurality of terminal ends (200*a*, 200*b*, 200*c*) on the inner sheath (150). Apart from that, the removable outer sheath (220) and cap (240) comprise the locking means (210*a*, 210*b*) for locking the inner sheath (150). Preferably, the present invention also comprises a tearable sealing member (260) comprising the two set of indicators (280*a*, 280*b*) for indicating the position of the pair of outer studs (170), the outer sheath inlet (230), the cap inlet (250) and the permanent locking means (210*b*) comprised on the safety injection needle assembly (110).

The exemplary implementation described above is illustrated with specific shapes, dimensions, and other characteristics, but the scope of the invention also includes various other shapes, dimensions, and characteristics. Also, the components as described above could be manufactured in various other ways and could include various other materials.

Various modifications to these embodiments are apparent to those skilled in the art from the description and the accompanying drawings. The principles associated with the various embodiments described herein may be applied to other embodiments. Therefore, the description is not intended to be limited to the embodiments shown along with the accompanying drawings but is to be providing broadest scope of consistent with the principles and the novel and inventive features disclosed or suggested herein. Accordingly, the invention is anticipated to hold on to all other such alternatives, modifications, and variations that fall within the scope of the present invention and appended claim.

Although the present invention has been described with reference to specific embodiments, also shown in the appended figures, it will be apparent for those skilled in the art that many variations and modifications can be done within the scope of the invention as described in the specification and defined in the following claims.

Description of the reference numerals used in the accompanying drawings according to the present invention:

| Reference Numerals | Description |
| --- | --- |
| 100 | Safety injection needle assembly |
| 110 | Injection needle |
| 120 | Hub |
| 130 | Stud |
| 140 | Receiving means |
| 150 | Inner sheath |
| 160 | Protruding surface |
| 170 | A pair of outer studs |
| 180 | Stud inlet |
| 190 | Slit |
| 200 | A plurality of terminal ends |
| 200a | First terminal end |
| 200b | Second terminal end |
| 200c | Third terminal end |
| 210 | Locking means |
| 210a | Temporary locking means |
| 210b | Permanent locking means |
| 220 | Outer sheath |
| 230 | Outer sheath inlet |
| 240 | Cap |
| 250 | Cap inlet |
| 260 | Sealing member |
| 270 | A pair of serrated lines |
| 270a | First serrated line |
| 270b | Second serrated line |
| 280 | Two set of indicators |
| 280a | First set of indicators |
| 280aa | First marking |
| 280ab | Second marking |
| 280ac | Third marking |
| 280b | Second set of indicators |
| 280ba | First pointer |
| 280bb | Second pointer |
| 280bc | Third pointer |

The invention claimed is:

1. A safety injection needle assembly (100), said safety injection needle assembly (100) comprising:

an injection needle (110) affixed to a hub (120), wherein said hub (120) having a stud (130) and a receiving means (140) for receiving a syringe, and said hub (120) is affixed to a proximal end of an injection site of said injection needle (110);

an inner sheath (150) having a slit (190) for receiving said stud (130), thereby positioning and retaining said injection needle (110) within said inner sheath (150); and an outer sheath (220) and a cap (240) for housing said inner sheath (150), wherein said inner sheath (150) houses said injection needle (110);

characterized in that;

said inner sheath (150) having a pair of outer studs (170);

said outer sheath (220) having an outer sheath inlet (230) and said cap (240) comprises a cap inlet (250), wherein said inlets configured to complement and removably engage with said pair of outer studs (170), thereby locking said inner sheath (150) with said outer sheath (220); and said slit (190) of said inner sheath (150) having a plurality of terminal ends (200*a*, 200*b*, 200*c*) for receiving said stud (130), thereby positioning said injection needle (110) and locking said stud (130) to retain said injection needle (110);

said outer sheath inlet (230) and said cap inlet (250) are separately and independently engageable with said inner sheath (150), each of said outer sheath inlet (230) and said cap inlet (250) independently comprising a temporary locking means (210*a*) and a permanent locking means (210*b*)

wherein engagement of said temporary locking means (210*a*) provides a releasable locking position, and engagement of said permanent locking means (210*b*) provides an irreversible end-use locking position, such that each of the outer sheath (220) and the cap (240) is selectively lockable to the same pair of outer studs (170) of said inner sheath (150).

2. The safety injection needle assembly (100) as claimed in claim 1, wherein said inner sheath (150) having a protruding surface (160) located between said pair of outer studs (170).

3. The safety injection needle assembly (100) as claimed in claim 2, wherein said outer sheath (220) and said cap (240) are separated by said protruding surface (160) of said inner sheath (150) in a pre-use position.

4. The safety injection needle assembly (100) as claimed in claim 1, wherein said inner sheath (150) comprising a stud inlet (180) for receiving said stud (130), whereby said stud inlet (180) being connected to said slit (190) of said inner sheath (150).

5. The safety injection needle assembly (100) as claimed in claim 1, wherein said plurality of terminal ends (200*a*, 200*b*, 200*c*) of said slit (190) including a first terminal end (200*a*), a second terminal end (200*b*) and a third terminal end (200*c*), whereby each of said first terminal end (200*a*), said second terminal end (200*b*) and said third terminal end (200*c*) of said inner sheath (150) having a locking means (210*a*, 210*b*) for locking said stud (130).

6. The safety injection needle assembly (100) as claimed in claim 5, wherein said first terminal end (200*a*) located at a distal end relative to a stud inlet (180) and said pair of outer studs (170) of said inner sheath (150).

7. The safety injection needle assembly (100) as claimed in claim 5, wherein a stud inlet (180) is located adjacent to said third terminal end (200*c*) of said slit (190); and wherein said stud inlet (180) and said second terminal end (200*b*) having a permanent locking means (210*b*) for locking said stud (130).

8. The safety injection needle assembly (100) as claimed in claim 7, wherein said safety injection needle assembly (100) comprising a sealing member (260) having a pair of tearable serrated lines (270) as an outermost layer, said sealing member (260) encircling a protruding surface (160) of said inner sheath (150), said outer sheath (220) and said cap (240) in a pre-use position.

9. The safety injection needle assembly (100) as claimed in claim 8 wherein said sealing member (260) is tearable into three sections along said pair of serrated lines (270), whereby said three sections are separately attached to said protruding surface (160) of said inner sheath (150), said outer sheath (220) and said cap (240), respectively.

10. The safety injection needle assembly (100) as claimed in claim 8 wherein said sealing member (260) has two sets of indicators (280*a*, 280*b*) for indicating positions of said outer sheath inlet (230), said cap inlet (250), said pair of outer studs (170) within said outer sheath inlet (230) and said cap inlet (250), said permanent locking means (210*b*) and said second terminal end (200*b*).

11. The safety injection needle assembly (100) as claimed in claim 10, wherein a first set of indicators (280*a*) of said two sets of indicators (280*a*, 280*b*) comprised on said sealing member (260) having three markings, whereby said three markings correspond to the positions of said outer sheath inlet (230), said pair of outer studs (170), and said cap inlet (250).

12. The safety injection needle assembly (100) as claimed in claim 10, wherein a second set of indicators (280*b*) of two sets of indicators (280*a*, 280*b*) comprised on said sealing member (260) having three markings, whereby said three markings correspond to said permanent locking means (210*b*) on said outer sheath inlet (230), said cap inlet (250) and said second terminal end (200*b*).

13. The safety injection needle assembly (100) as claimed in claim 1, wherein said temporary locking means (210*a*) comprising a plurality of projections.

14. The safety injection needle assembly (100) as claimed in claim 1, wherein said permanent locking means (210*b*) comprising a unidirectional lock.

* * * * *